United States Patent [19]

Kaji

[11] Patent Number: 4,689,320

[45] Date of Patent: Aug. 25, 1987

[54] METHOD FOR INHIBITING PROPAGATION OF VIRUS AND ANTI-VIRAL AGENT

[76] Inventor: Akira Kaji, 1-9, Daimoncho 1-chome, Higashikurume-shi, Tokyo, Japan

[21] Appl. No.: 661,204

[22] Filed: Oct. 15, 1984

[30] Foreign Application Priority Data

Oct. 17, 1983 [JP] Japan .................................. 58-192350
Mar. 16, 1984 [JP] Japan .................................. 59-49321

[51] Int. Cl.$^4$ ............................................. A61K 31/70
[52] U.S. Cl. ......................................... 514/44; 536/27; 536/28; 536/29
[58] Field of Search ................. 536/27, 28, 29; 514/44

[56] References Cited

U.S. PATENT DOCUMENTS

| | | | |
|---|---|---|---|
| 4,393,201 | 7/1983 | Curtis et al. | 536/28 |
| 4,433,140 | 2/1984 | Seliger et al. | 536/28 |
| 4,464,359 | 8/1984 | Suhadolnik et al. | 536/27 |
| 4,511,713 | 4/1985 | Miller et al. | 536/28 |

FOREIGN PATENT DOCUMENTS

WO83/01451 4/1983 PCT Int'l Appl .................... 536/27

Primary Examiner—Johnnie R. Brown
Attorney, Agent, or Firm—Birch, Stewart, Kolasch & Birch

[57] ABSTRACT

Described is a method for inhibiting propagation of virus which comprises delivering one or more oligodeoxynucleotides or polydeoxynucleotides to a place where a messenger RNA (mRNA) generated on propagation of the virus exists, characterized in that the oligodeoxynucleotides or polydeoxynucleotides are identical in DNA sequence with a portion of the structure of DNA hybridizable to the mRNA, the structure being capable of hybridizing to the mRNA. Also described is an anti-viral agent which comprises an effective amount of one or more oligodeoxynucleotides or polydeoxynucleotides with a conventional liquid vehicle or excipient, characterized in that the oligodeoxynucleotides or polydeoxynucleotides are identical in DNA sequence with a portion of the structure of DNA hybridizable to an mRNA generated on propagation of the virus, the structure being capable of hybridizing to the mRNA. The method and the agent can widely be applied to the treatment of viral diseases.

22 Claims, 4 Drawing Figures

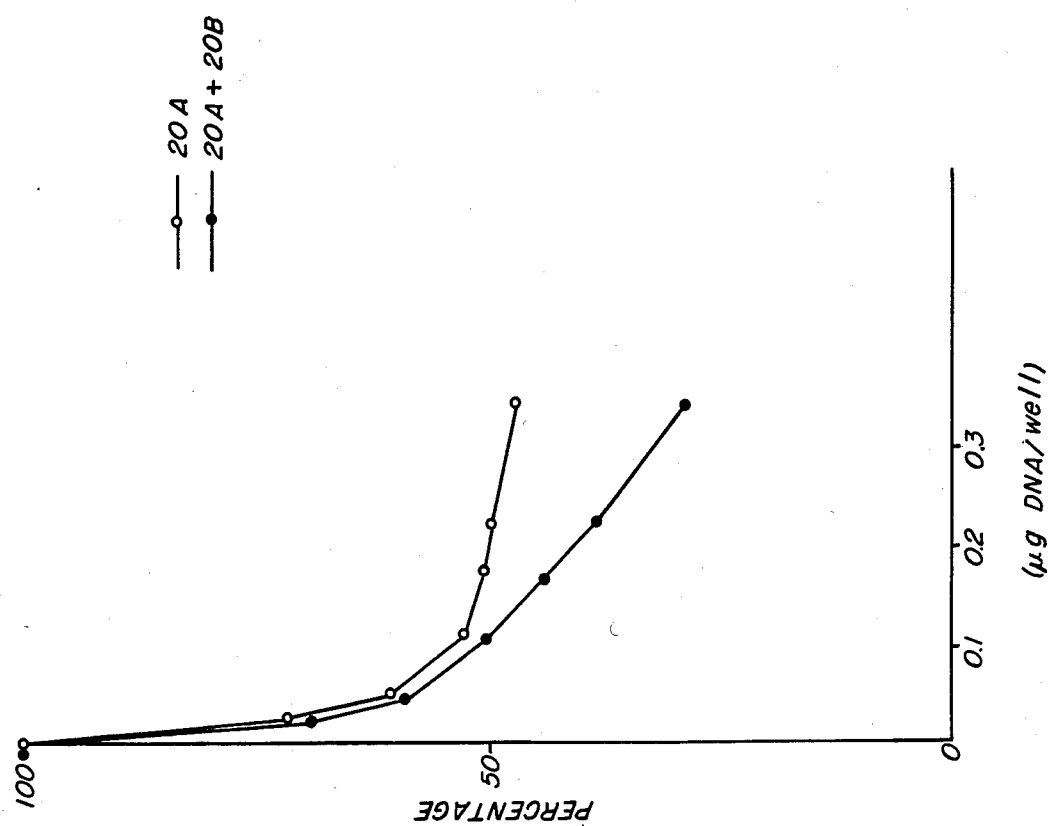

METHOD FOR INHIBITING PROPAGATION OF VIRUS AND ANTI-VIRAL AGENT

BACKGROUND OF THE INVENTION

1. Field of the Invention:

The present invention relates to a method for inhibiting propagation of virus and to an anti-viral agent. More particularly, the present invention relates to a method for inhibiting propagation of virus wherein a specific oligo- or polydeoxynucleotide is applied to the place infected by virus as well as an anti-viral agent containing a specific oligo- or polydeoxynucleotide.

2. Description of the Prior Art:

At the early stage of the remedy of diseases caused by virus, chemically synthesized medicines and antibiotics were employed as anti-viral agents to inhibit the propagation of virus. In the case of the chemically synthesized medicines, however, their anti-viral spectrum is rather narrow and harmful side-effects brought about by such medicines often come into question. In the case of the antibiotics, on the other hand, there is a detrimental drawback that development of new-type antibiotics are always required in addition to efforts to reduce any harmful side-effect manifested by antibiotics since virus becomes resistant to the antibiotics used and finally becomes immune thereto with the lapse of time.

With the recent development of biotechnology, especially genetic engineering, identification of the structural genes of virus has become a great theme of research among those engaged in the study of microorganisms. In 1977, S. C. Inglis et al. reported the in vitro translation of cytoplasmic RNA extracted from chick embryo fibroblasts infected with influenza A virus in a wheat germ cell-free protein-synthesizing system, with the result that the synthesis of the virus-specific polypeptide corresponding to the hybridized v-RNA segment is reduced [Virology 78, 522-536 (1977)]. However, the experiments referred to in this reference are carried out with a cell-free system having no relation to the study of medicine. Such structural gene identification is also reported by B. M. Paterson et al. in Proc. Natl. Acad. Sci., U.S.A., 74, 4370-4374 (1977). The experiments by Paterson et al. are also carried out with a cell-free system. In these two references, what is used for inhibiting the synthesis of protein is an enormous genetic structure such as RNA itself extracted from the influenza virus in the firstly mentioned reference or rabbit β globin clone PβG1 in the secondly mentioned reference. Such an enormous structure could not be expected to inhibit the intracellular synthesis of protein.

In 1978, P. C. Zamecnik et al. reported that a tridecamer oligodeoxynucleotide complementary to the reiterated 3'- and 5'-terminal nucleotides of Rous sarcoma virus (RSV) is an efficient inhibitor of the synthesis of protein specified by the viral RNA in wheat cell-free system [Proc. Natl. Acad. Sci., U.S.A., 75, 285-288 (1978)] and in an in vitro tissue culture system [ibid. 75, 280-284 (1978)]. Concerning the first reference, the cell-free system is still used as before but some improvement is recognized in respect of using a DNA with a smaller molecular structure for inhibiting the translation of protein. In the second reference, experiments are carried out using the tridecamer in a tissue culture system for inhibiting replication of virus and transformation of cells. The DNA used in these references for inhibiting the replication and the transformation is selected from a region other than a specific coding region and is not desirable. In the same year, N. D. Hastie et al. also reported that hybridization of globin mRNA to its corresponding cDNA was found to specifically inhibit translation of the mRNA in a cell-free system [ibid. 75, 1217-1221 (1978)]. Novel in this reference is only that a certain coding region of DNA is selected for inhibition of the translation by hybridization of mRNA. However, the experiments referred to therein were still carried out in a cell-free system. There has been a demand for developing medicines based on this theory since publication of these references in 1978. Hitherto, however, there has been reported no reference in connection with a device for applying this theory practically to experiments in vivo.

In 1983, a PCT patent application relating to oligonucleotide therapeutic agent and methods of making same (Molecular Biosystems INC., Intl. Publn. No. WO83/01451) was published. However, what is disclosed in this application is a mere statement that (-)-strand DNA selected from a certain coding region inhibited SV 40 transformed cell.

Although the expression "in vivo" is often used in Example 1 of this reference, the descriptions referred to therein are, in view of the context, apparently suggestive of the experiments in vitro cell culture system. Even if such experiments in vitro were deemed as experiments in vivo, they lack concrete conditions thereof and are nothing but a mere mention of expectation of desirable effects. Anyway, this reference suggests for the first time application of RNA-DNA hybridization technique to a medicine but lacks detailed descriptions for substantiating utility as medicines and is nothing more than a mere aggregation of the knowledges manifested at that stage. Thus, what is taught in this patent application involves nothing beyond the technical level disclosed in the references described above.

Under the circumstances mentined above, there is a great demand for providing an entirely new type of anti-viral agent by developing the theory of inhibiting mRNA translation of virus on the basis of the RNA-DNA hybridization technique to realize inhibition of the propagation of virus in vivo.

BRIEF SUMMARY OF THE INVENTION

Accordingly, it is an object of the present invention to provide a method for inhibiting propagation of virus, which comprises delivering the specific oligo- or polydeoxynucleotide to the place infected by the virus.

It is another object of the present invention to provide a new type of an anti-viral agent comprising a specific oligo- or polydeoxynucleotide.

It is still another object of the present invention to provide the use of an oligo- or polydeoxynucleotide identical in DNA sequence with a portion of the structure of DNA hybridizable to an mRNA generated on the propagation of virus, the structure being capable of the hybriding to the mRNA, for inhibiting the propagation of the virus.

Other objects, features and advantages of the present invention will become apparent more fully by the following description.

Further, the present invention can more fully be understood from the following description in conjunction with the accompanying drawings in which:

FIG. 1 is a graph showing the result of experiments which demonstrate the inhibitory effects of the oligodeoxynucleotide (the 20 A) on the cytopathic effects of HSV-1.

FIG. 3 is a graph showing the effect of a certain combination of the oligodeoxynucleotides for the inhibition of multiplication of virus and the pathogenic effect thereof as compared with a single oligodeoxynucleotide used therein.

DETAILED DESCRIPTION OF THE INVENTION

Figure 4:
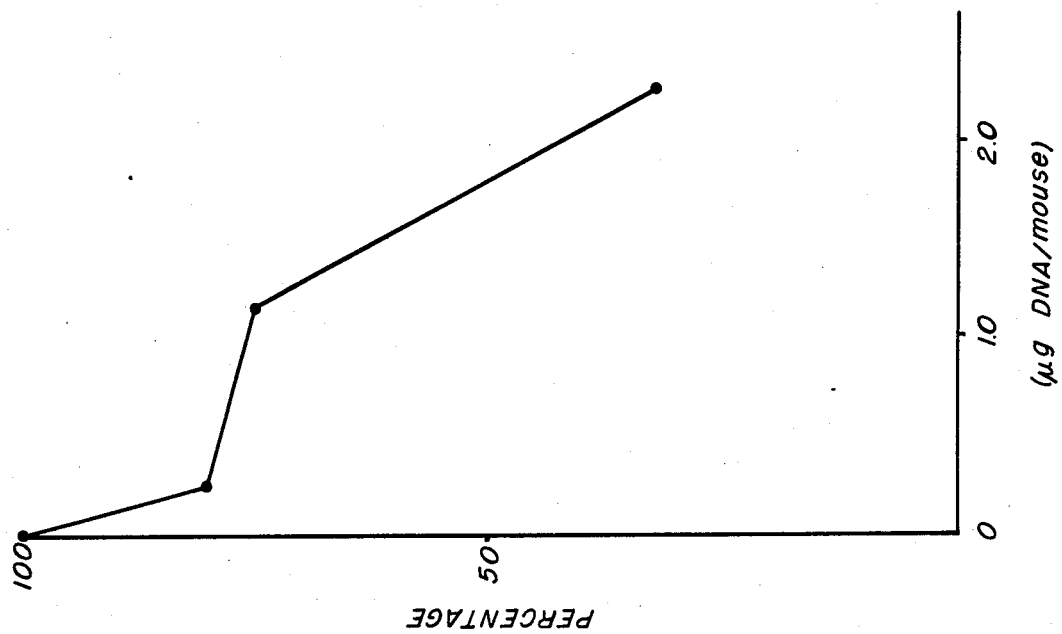
FIG. 4 is a graph showing the result of experiments which were designed to demonstrate the in vivo effectiveness (in a living animal) of the anti-viral agent of this invention.

The present inventor has found that when an oligodeoxynucleotide or polydeoxynucleotide identical in DNA sequence with a portion of the structure of DNA hybridizable to mRNA generated on the propagation of virus is delivered to the place where the mRNA exists, the structure being capable by hybridizing to the mRNA, the propagation of the virus is effectively inhibited. By administering the oligo- and polydeoxynucleotides to animals infected by a virus, the inventor has succeeded in providing an anti-viral agent capable of effectively inhibiting the propagation of virus in vivo. The present invention has been accomplished on the basis of the above finding.

As described previously, the hybridization of viral or globin RNA to the corresponding DNA for inhibition of the synthesis of protein was known from the references mentioned above. However, the majority of experiments relating thereto was carried out in a cell-free system except Zamecnik's second reference (Proc. Natl. Acad. Sci., U.S.A., 75, 280–284) and Molecular Biosystem Inc. reference (PCT, Intl. Publn. No. WO83/01451) wherein inhibition of the propagation of virus in an in vitro cell culture system is described. In the Zamecnik's in vitro experiments, however, DNA is selected from a region other than a specific coding region for the virus. By the term "coding region" is meant herein regions of viral genes which code for (determine the amino acid sequence of) viral proteins and which undergo the transcription by an RNA polymerase to produce mRNA. On the other hand, the Molecular Biosystem Inc. reference lacks disclosures on concrete conditions for the experiments. The present inventor has carried out extensive researches and experiments both in vitro and in vivo systems using specific oligodeoxynucleotides or polydeoxynucleotides selected from a specific coding region and made it possible for the first time to develop the theory of inhibiting the propagation of virus on the basis of the RNA-DNA hybridization technique to a practically utilizable level of therapy, thereby enabling the use of the oligodeoxynucleotides or polydeoxynucleotides as a medicine for inhibiting the propagation of virus. Thus, the present invention is quite different from the known arts in respect of the two concepts; the selection of DNA from a specific coding region which is hybridizable to mRNA of virus and the use of a single stranded deoxynucleotide having a short chain length as the DNA selected from the specific coding region, and is also distinguished by developing the above concepts to a practically utilizable level by way of abundant in vivo experiments.

In accordance with the present invention, therefore, there is provided a method for inhibiting the propagation of virus which comprises delivering one or more oligodeoxynucleotides or polydeoxynucleotides to a place where an mRNA generated on the propagation of virus exists, characterized in that the oligodeoxynucleotides or polydeoxynucleotides are identical in DNA sequence with a portion of the structure of DNA hybridizable to the mRNA, the structure beihg capable of hybridizing to the mRNA.

In accordance with the present invention, there is also provided an anti-viral agent which comprises an effective amount of an oligodeoxynucleotide or polydeoxynucleotide with a conventional liquid vehicle or excipient, characterized in that the oligodeoxynucleotide or polydeoxynucleotide is identical in DNA sequence with a portion of the structure of DNA hybridizable to an mRNA generated on the propagation of virus, the structure being capable of hybridizing to the mRNA.

The inventor first discovered that, when a synthetic RNA as mRNA is translated in an in vitro protein synthesis system, the protein synthesis is inhibited by an oligodeoxynucleotide which hybridizes to the synthetic RNA. (See Example 25 described below).

Oligodeoxynucleotides which do not hybridize to the RNA did not inhibit the protein synthesis in this system.

The inventor secondly discovered that oligodeoxynucleotides of the (−)-strand sequence of α-globin or β-globin DNA inhibit the translation of the corresponding mRNA. (See Example 26 described below).

As a result of the experiment, it was found that α-globin DNA specifically inhibits the translation of α-globin mRNA in the in vitro system. Furthermore, it was found that the α-globin DNA inhibits specifically the translation of β-globin mRNA in this system. In addition, when DNA which does not hybridize to the α-globin mRNA was used, the production of α-globin was not inhibited. In a similar manner, the β-globin production was not inhibited by DNA which does not hybridize to β-globin mRNA. It was further found that not only DNA with a long chain but also oligodeoxynucleotides have a strong inhibitory effect in this system, due to hybridization.

On the basis of these experiments, further experiments concerning herpes simplex virus (HSV) infection were performed. When DNA or oligodeoxynucleotides which can hybridize to the immediate early mRNA of HSV were given to cells infected by this virus, it was found that the number of syncytia (a plaque like hole which was made by HSV due to the fusion of infected cells) caused by HSV was remarkably reduced.

In the above experiments, $CaCl_2$ and Ca phosphate were used together with the DNA to stimulate penetration of the DNA into cells. In separate experiments, however, it was found that the oligodeoxynucleotide can be taken up even without these calcium salts, and thus inhibits the propagation of HSV and its cytopathic effects. (See Example 7 described below).

From these experiments, it became clear that the minus strand DNA, which hybridizes to an mRNA of HSV-1 inhibits syncytium formation by this virus. Based on this observation, the inventor further applied such DNA to mice infected with HSV and demonstrated that such DNA can be used as an anti-viral agent in vivo for the treatment of viral diseases.

Noteworthy here is that only the negative strand DNA specific for the mRNA of that particular viral gene is used as an effective component in the agent and method of the present invention. Therefore, the biosynthesis of cellular protein programmed by other mRNA's should not be influenced by using the DNA mentioned above.

There are two groups of viruses; DNA viruses (herpes simplex virus, adeno virus, vaccinia virus, etc.) and RNA viruses (influenza virus, rhino virus, and polio virus, etc.). RNA viruses either carry single stranded RNA or double stranded RNA as a genome. Single stranded RNA viruses are classified into those carrying plus stranded RNA and those carrying minus stranded RNA as their genome.

Viral proteins always have to be synthesized by translation of a viral mRNA which is a plus stranded RNA. Viruses with a double stranded DNA genome produce mRNA (plus strand) from their minus stranded DNA strand. As to the double stranded RNA viruses, the mRNA (plus stranded) is produced from the minus stranded RNA. The genome of plus stranded RNA viruses itself functions as a mRNA while the minus stranded RNA viruses use their RNA as templates for the production of plus stranded RNA (mRNA).

According to this invention, the translation of a viral mRNA and thus the synthesis of viral proteins is, independent from the mechanism of the synthesis of mRNA, inhibited by a hybridizing minus strand DNA. Although only examples wherein herpes simplex virus (double stranded DNA virus) and influenza virus (single stranded RNA virus) were used are given herein, the present invention can widely be applied for inhibiting in general the propagation of viruses. Thus, propagation of viruses such as influenza virus, adeno virus, leukemia virus, dengue virus, rabies virus, hepatitis virus, measles virus, encephalitis virus, parainfluenza virus, rhino virus, yellow fever virus and EB virus can be inhibited by the method and the agent of this invention.

Thus, the present invention can widely be utilized for the prevention or treatment of various diseases of animals and plants caused by viruses. The respective pharmaceutical compositions are thus very useful in various fields.

According to the method of the present invention, the propagation of RNA or DNA viruses and their cytopathic effects can be stopped without influencing host cells. Further, infection of uninfected host cells can be prevented by the method of this invention. It was found by the inventor that oligodeoxynucleotides alone hybridizing to the immediate early mRNA of herpes simplex virus have neither effect on normal uninfected baby hamster kidney cells (BHK cells) nor effect on mice. Therefore, it was concluded that the oligodeoxynucleotides have neither harmful effect on normal cells and animals nor influence on the growth rate of these cells at all.

The negative stranded deoxynucleotides used in this invention may be obtained by enzymatic hydrolysis of DNA, denaturation and subsequent separation by affinity chromatography. Alternatively, synthetic negative stranded oligodeoxynucleotides can be used. Thus, it is evident that the negative stranded deoxynucleotides used in the experiments described herein can be obtained by a variety of methods.

In the cloning of RNA virus gene, the reverse transcriptase may be used. In some cases, viral DNA present in infected cells and originated from the RNA virus genome can be used. As a cloning vehicle, for example, lambda phage (Charon phage) or plasmid pBR 322 can be used as vector. For obtaining a single stranded (−) DNA, M 13 phage will be used as vector. According to the present invention, the cloned DNA of coding region of any part of the total viral genomes may be used. However, early or immediate early genes whose expression is observed in early stages of infection are particularly desirable for the prevention of virus propagation and the concomitant cytopathic effects.

A recombinant M 13 phage containing a negative stranded viral DNA or a recombinant DNA vector containing the double stranded viral DNA can be produced by growing large quantities of E. coli harboring these vectors or E. coli infected with the M 13 phage. Vectors containing the viral genes were isolated and subjected to restriction endonuclease for excision of the viral genes. The mixture of the excised viral genes and the vector DNA was then subjected to agarose gel electrophoresis or sephadex column chromatography for separating the virus gene DNA from the vector DNA. The DNA molecules thus obtained were shortened by partial digestion with DNA restriction endonuclease or ultrasonic treatment. The chain length of the viral DNA fragments was adjusted to anywhere between 9 and 100 nucleotides by isolating these DNA strands by gel electrophoresis and sephadex chromatography.

It is to be noted that only the negative strand of viral DNA is effective for the inhibition of the viral protein synthesis. When the DNA of vectors are such as pBR 322 or lambda phage as the replicating form of M 13 phage it is a double stranded DNA. Therefore, this double stranded DNA has to be converted to a single stranded DNA followed by isolation of negative stranded DNA. For this purpose, various methods can be used. For example, DNA is denatured by heating to 100° C. for 10 minutes and rapidly cooled.

From a mixture of the separated negative and positive strand DNA, the negative stranded DNA may be isolated, for example, by affinity chromatography. For this purpose, the positive stranded DNA is first prepared by cloning into M 13 phage. This is then conjugated to a support material for chromatographic use. A mixture of negative and positive strand DNA is then passed through the conjugated positive DNA column. The negative strand DNA is bound to this column while the positive strand DNA passes through the column. The bound negative strand DNA is then eluted from the column.

In an alternative method for obtaining the negative strand DNA, it is synthesized chemically in the form of oligo- or polydeoxynucleotides by a proper synthetic method in organic chemistry.

In case of the herpes simplex virus, for example, one of the immediate early DNA genes, Vmw 175, has a double strand consisting of a plus DNA (5'-ATG.GCG.TCG.GAG . . . ) and a minus DNA (3'-TAC.CGC.AGC.CTC . . . ). Only the minus DNA having a sequence beginning with TAC can hybridize to an mRNA of Vmw 175. Thus, any of the DNA which is identical in a partial structure with the minus DNA strand has to be selected and synthesized as an oligodeoxynucleotide. The influenza virus genome includes the hemagglutinin gene and NS (non-structural) genes. Since the hemagglutinin gene of different serotypes of influenza virus vary in their RNA sequence, the sequence of a single stranded DNA which hybridizes to the mRNA of the NS genes is preferred for the purpose of the present invention. (−)Strand DNA hybridizing to the mRNA from the NS genes is more desirable than that hybridizing to the mRNA from the hemagglutinin gene because the hemagglutinin gene mutates very frequently and the (−) strand DNA hybridizing to the mRNA from the hemagglutinin gene of a single strain of influenza virus may not crosshybridize to the mRNA from the hemagglutinin gene of another serotype strain of influenza virus.

Further explanation for the NS-1 gene of influenza virus is given, for example, by Lamb et al., [Cell 21 47 (1980)]. The DNA sequence which hybridizes to an mRNA from NS-1 gene is 5'- . . . ACT.TGA.CAC-.AGT.GTT.GGA.ATC.CAT . . . -3'. Therefore, the whole or a part of this sequence may be selected and synthesized.

The present invention can also be applied to viruses related to in the field of poultry and livestock industries, such as Rous Sarcoma Virus. For example, the inhibition of expression of one of the genes gag., pol. and env. of this virus should inhibit the propagation of this virus. If, for example, the inhibition of the expression of the gag. gene by a hybridizing DNA molecule is desired, an oligo- or polydeoxynucleotide having a part of the sequence 5'- . . . AAT.CAT.CTT.TAT.GAC.GGC.TTC . . . -3' can be selected and synthesized, taking into consideration the RNA sequence of P 19 which is a part of the gag. gene.

It is evident from the foregoing explanations, that in principle, for the inhibition of virus propagation by a single stranded minus strand DNA, effective single stranded DNA should be selected, which hybridizes to an mRNA of this virus.

In general, the term "oligodeoxynucleotide" stands for a molecule having a smaller number of deoxynucleotide units while the term "polydeoxynucleotide" for a molecule having a larger number or deoxynucleotide units. In this invention, for example, the number of nucleotide units of the oligodeoxynucleotides is usually up to 25. Thus, deoxynucleotides having more than 25 deoxynucleotide units may be designated as "polydeoxynucleotides" in this invention.

The anti-viral agents of the present invention containing the oligo- and/or polydeoxynucleotide with a suitable liquid vehicle or excipient and optionally an auxiliary additive or additives are prepared in the form of liquid preparations, injections, suppositories, etc. according to known methods. On prescription, the desired oligodeoxynucleotides and polydeoxynucleotides can be used singly or in combination with other pharmacologically active ingredients. In this case, it is obvious that these other ingredients should not adversely affect the antiviral activity of the oligo- and polydeoxynucleotides.

The oligo- and polydeoxynucleotides can be processed, if desired, to externally applicable preparations such as cream, ointment, liquid and plaster by mixing the oligo- and polydeoxynucleotide as the active ingredient with a suitable inert vehicle or excipient.

The liquid vehicles or excipients as well as the optional auxiliary additives used in the anti-viral agents of the present invention are conventional ones and commercially available.

Illustrative of the liquid vehicles, excipients and auxiliary additives useful for the preparation of the anti-viral agents are, for example, distilled water for injection use, physiological saline, an aqueous solution of dextrose, vegetable oils for injection use, propylene glycol, polyethylene glycol and benzyl alcohol (for injections and liquid preparations); vaselin, vegetable oil, animal fat and polyethylene glycol (for externally applicable preparations); and isotonic agents, dissolution promoting agents, stabilizers, colorants, antiseptic agents, soothing agents and the like additives (as usual auxiliary additives to pharmaceutical preparations). In case of the injection preparations, the active ingredient may desirably be dissolved in sterilized liquid vehicles. It is evident that the above mentioned various liquid vehicles, excipients and auxiliary additives should not inhibit nor disturb the anti-viral action of the oligo- and polydeoxy-nucleotides.

The oligo- and polydeoxynucleotides of the present invention are processed with the vehicles or excipients referred to above and optionally together with auxiliary additives referred to above according to known methods. Injection preparations and suppositories may usually contain 1–10 mg of the oligo- and polydeoxynucleotides per ampoule or capsule. For human patients, the daily dose is about 0.1–1,000 mg, preferably 1–100 mg (from 10–20 μg/kg to 1000–2000 μg/kg body weight). However, the particular dose for each patient depends on a wide range of factors, for example, on the effectiveness of the particular oligo- or polydeoxynucleotide used, on the age, weight, general state of health, sex, on the diet, on the time and mode of administration, on the rate of elimination, combination with other medicaments jointly used and severity of the particular diseases to which the therapy is applied.

The anti-viral agents of the present invention are administered intravenously or applied directly to the part of the body of a patient infected by virus so that the oligo- or polydeoxynucleotide may effectively be delivered to the infected part.

The present invention will now be illustrated in more detail by the following examples and referential examples.

Examples 1–5 relate to the preparation of the oligo- and polydeoxynucleotides used in the present invention.

EXAMPLE 1

Herpes simplex virus DNA was isolated by phenol-chloroform extraction. The isolated DNA was digested by the restriction enzyme BamHI.

The digested DNA was then mixed in the presence of T 4 phage ligase with pBR 322 plasmid DNA previously treated with BamHI.

The resulting mixture containing ligated plasmids was given to *E. coli* and the bacteria which contains the recombinant plasmid was selected by incubating them on agar plates containing ampicillin to form colonies and screening them for tetracycline sensitivity. Among the tetracycline sensitive colonies, those bacteria having the herpes simplex virus DNA were selected by the filter hybridization method with $^{32}P$ labelled herpes viral DNA as a probe. To obtain the recombinant plasmid DNA, $2\times10^6$–$10^7$ *E. coli* cells containing the recombinant plasmid were placed in 2 ml TSB (Tryptose Soy Broth).

The inoculated medium was shaken in a 20 ml test tube at 37° C. for about 15 hours until the optical absorption (Optical density: OD) of the culture medium at 540 nm reached 0.5 ($OD_{540}=0.5$). At this point chloramphenicol was added to a final concentration of 100 μg/ml and incubation was continued for 15 hours.

The bacteria suspension was then centrifuged and the pellet was resuspended in a buffer containing 25% sucrose and 50 nM tris HCl (pH 8.0). The suspension was left standing at 0° C. for 5 minutes. To this suspension, 4 ml of Triton X 100 was added and the resulting viscous solution was centrifuged for 30 minutes at 0° C. at 30,000 g. To the supernatant of this solution (8 ml), 8 g of CsCl, 1 ml of a solution of ethidium bromide (5 μg ethidium bromide/ml) were added. The mixture was further centrifuged for 48 hours at 100,000 g. The crude plasmid fraction obtained after this centrifugation was mixed with 2 volumes of isopropyl alcohol, and left standing for a few minutes. The upper layer was removed and the solution containing DNA was dialized against 0.1M tris HCl and 10 mM EDTA (pH 8.0) overnight.

The dialized solution was concentrated and the solution containing 200 μg DNA was treated with an excess amount of restriction enzyme (BamHI). The DNA digest was separated by agarose electrophoresis and the DNA of herpes simplex virus was isolated from the gel by the electroelution method. The DNA was further digested partially by DNase and heated to 100° C. for 10 minutes followed by rapid cooling. Thus, DNA having chain lengths of 9 to 100 oligodeoxynucleotides were obtained.

EXAMPLE 2

The replicative form of M 13 phage DNA (double stranded DNA) was cut with BamHI. This digested M 13 DNA was mixed with herpes simplex virus DNA which had been digested by BamHI and isolated as described above. They were ligated with T 4 phage ligase. E. coli were transfected with the ligated DNA in the presence of CaCl$_2$ The transfected bacteria were plated on agar plates using a top agar which contained IPTG (isopropyl-β-D-thio-galactopyranoside) an X-gal (an indicator). Recombinant M 13 phages containing herpes simplex virus DNA form colorless phage plaques within 24 hours. M 13 phages without insertion form blue plaques. Therefore, the colorless phage plaques were chosen. To select recombinant M 13 phage which contains (−) strand HSV DNA, phages were checked for their capacity to hybridize with labelled (+) HSV DNA which is chemically synthesized. In this manner were selected M 13 phages containing a part of the (−) strand of HSV DNA were selected. The desired recombinant M13 phage was increased in quantity and a single stranded DNA was isolated from this phage. For further purification of the single stranded HSV DNA, M 13 phage DNA can be removed from this mixture by restriction enzyme digestion in the presence of certain oligodeoxynucleotides. Alternatively the DNA mixture, without purification can be partially digested with DNase and oligodeoxynucleotides having chain lengths between 9 and 100 can be isolated.

EXAMPLE 3

A DNA synthesizer (Applied Biosystem Company) was used to synthesize minus strand DNA of the immediate-early gene (Vmw 175 or ICP 4) of herpes simplex virus. In this example, the DNA sequence 3'-CGC.AGC.CTC.TTG.TTC.GTC.GC-5' was synthesized which hybridizes with mRNA of Vmw 175. This deoxynucleotide is eicosamer and is referred to hereinafter simply as the 20 A.

EXAMPLE 4

A DNA synthesizer (Applied Biosystem Company) was used to synthesize minus strand DNA of the immediate-early gene (Vmw 12) of herpes simplex virus. In this example, the DNA sequence 3'-GCA.CCC.GG-G.ACC.TTT.ACC.GC-5' was synthesized which hybridizes with mRNA of Vmw 12. This deoxynucleotide is eicosamer and is referred to hereinafter simply as the 20 B.

EXAMPLE 5

A DNA synthesizer (Applied Biosystem Company) was used to synthesize minus strand DNA of the NS 1 gene of influenza virus. In this example, the DNA sequence 3'-CTA.AGT.TTG.TGA.CAC.AGT.TCA-5' was synthesized which hybridizes with mRNA of NS 1. This deoxynucleotide is heneicosamer and is referred to hereinafter simply as the 20 C.

EXAMPLE 6

This example relates to an experiment by which it is confirmed that the oligodeoxynucleotide inhibits the synthesis of virus protein in vitro.

Table 1 illustrates the inhibitory effect of the 20 A on Vmw 175 formation and the corresponding cytopathic effect (Syncytium Formation) of HSV 1.

TABLE 1

| The 20 A/well | Relative amounts of Vmw 175 | Relative Cytopathic effects (Syncytium) |
|---|---|---|
| — | 1 | 1 |
| 33.6 μg | 0.48 | 0.35 |

BHK cells (1.5×10$^5$) were plated in each well (1.5 cm in diameter) of a Limbro dish and MEM with 10% calf serum was added. The cells were then incubated in a 5% CO$_2$ atmosphere at 36° C. Subsequently, the cells were infected with 5 moi of HSV-1 in the presence or absence of the 20 A. After 5 hours, the medium was removed. The cells were then contacted for 1 hour with $^{35}$S-methionine (100 μCi/μl) and the 20 A disrupted, and proteins were analyzed by polyacrylamide gel electrophoresis followed by autoradiography. For evaluation of the relative cytopathic effect, experimental conditions were identical to the above except that the numbe of syncytia was counted 13 hours after the infection. No decrease of cellular protein synthesis was observed under these conditions.

EXAMPLE 7

This example relates to an experiment by which it is confirmed that the oligodeoxynucleotide is taken up by cells.

This experiment indicates that the single stranded oligodeoxynucleotide 20 A is indeed permeable into cultured cells. BHK cells (baby hamster kidney cells; 4.4×10$^5$ cells) were infected with 7.6×10$^4$ PFU of HSV-1/ml. Control cells were not infected but were given the same amount of the culture medium. The cells were incubated for 3 hours in a CO$_2$ incubator at 37° C. After the incubation, the cells were exposed to 7.66 p moles of the $^{32}$P labelled 20 A. After the exposure to the labelled 20 A, the culture medium was removed and the cells were washed twice with 0.3 ml of PBS.

The cells were then left for 30 minutes at 36° C. in a solution containing 0.1 M NaCl, 33 μM ZnCl$_2$, 3360 units of nuclease S1 and 33.3 mM sodium acetate buffer (pH 4.5).

Subsequently, the cells were washed twice with the buffer described above but without nuclease S1. The washed cells were disrupted in 0.3 ml of a solution containing 10 mM EDTA, 0.6 % sodium dodecyl sulfate, and 10 mM tris-HCl buffer (pH 7.5). At this point, TCA-insoluble, nuclease S1-sensitive, radioactive 20 A was measured. It was found that at least $4.68 \times 10^3$ molecules of the 20 A had been taken up per cell during the exposure period of 8 hours. The actual amount is probably 10 times higher than this value because of the rapid hydrolysis of $^{32}P$ terminal phosphates.

The following Example 8 illustrates that the 20 A has an inhibitory effect on the propagation of virus.

EXAMPLE 8

Approximately $1.5 \times 10^5$ BHK cells were plated per each well (1.5 cm in diameter) of a Limbro dish. These cells were incubated in 5% $CO_2$ at 36° C. for 48 hours and infected with HSV-1 ($7.6 \times 10^4$ PFU/ml) in 160 µl of MEM. The infection was carried out for 3 hours at 36° C. in 5% $CO_2$. After the infection the 20 A was applied to the infected cells. After 8 hours exposure, the medium was changed to normal MEM with 10% calf serum. At 15 hours after the infection, the culture fluid was harvested and virus titer was measured. The results are shown in Table 2 below.

TABLE 2

| Amount of the 20 A/well | Relative amount of virus |
|---|---|
| 0 | 100 |
| 0.112 µg | 45 |
| 0.224 µg | 35 |

Examples 9-13 relate to experiments by which it is confirmed that the oligodeoxynucleotide inhibits destruction of animal cells by virus in vitro.

EXAMPLE 9

(a) Approximately $1.5 \times 10^5$ BHK cells were placed in each well (1.5 cm in diameter) of a Limbro dish for cell culture. The cells were incubated for 47 hours at 36° C. in 5% $CO_2$ and then infected with 160 µl of HSV-1 ($7.6 \times 10^4$ PFU/ml) for 3 hours at 36° C. To these infected cells, a complex of calcium phosphate and the 20 A in various amount was added. $Ca^{++}$ concentration of the media varied from 1.36 mM to 24.8 mM depending on the concentration of the 20 A. The complex was prepared as described by Ruddle's group (Loiter et al, Proc. Nat. Acad. Sci. 79 422, 1982). The infected cells were exposed to the 20 A for 8 hours. The culture medium was then removed and replaced with a normal culture medium without the 20 A and the cells were grown for additional 13 hours.

(b) The control cells were treated identically except for the addition of the 20 A (Ca-phosphate control).

(c) As an additional control, an infected culture was prepared which was treated with neither Ca-phosphate nor the 20 A (virus control). The tissue culture cells prepared above (a), (b), (c), were fixed, stained and the number of syncytia was counted.

The result of this experiment is shown in FIG. 1, wherein the axis X (abscissa) stands for the amount of DNA in terms of µg added to each well (i.e. "µg DNA/well") and the axis Y (ordinate) for the number of syncytia in terms of percentage (i.e. "% number of syncytia") formed in a cell culture as compared with the value obtained in the case of the experiment (c) for "virus control", the value in this case being set always as 100 and wherein a plot drawn by a solid line (a) (— • —) shows the result obtained with the experiment (a) while a plot drawn by a dotted line (b) (— ○ —) shows the result obtained with the experiment (b). As shown in FIG. 1, the syncytium formation was remarkably inhibited by the 20 A. Calcium phosphate or calcium chloride did not influence the number of the syncytia.

EXAMPLE 10

(a) Approximately $1.5 \times 10^5$ BHK cells were placed per well (1.5 cm in diameter) of a Limbro dish. The cells were incubated at 36° C. for 47 hours under 5% $CO_2$. To these cells were added 160 µl of HSV-1 ($7.6 \times 10^4$ PFU/ml) and infections were allowed for 3 hours at 36° C. To these infected cells various amounts of the 20 A were added in the form of a calcium chloride complex in the final $Ca^{++}$ concentration of 4.55 mM. The treatment was continued for 8 hours. The cells were then further incubated for 14 hours.

(b) In addition, an identical culture as described above (a) was prepared except that an oligodeoxynucleotide which has no relation with HSV-1 sequence 5'-CAC.GAC.AGA.GGG.CGA.-3' was prepared and incubated. All other conditions were identical with the case of (a).

(c) A similar culture in which the 20 A was left out was prepared and incubated under the same condition as above. This is referred to herein as "virus control".

The cells described above in (a), (b) and (C) were fixed, stained and the number of syncytia was counted. The results of this experiment are shown in FIG. 2, wherein the axis X (abscissa) stands for the amount of DNA in terms of µg added to each well (i.e. "µg DNA/well") and the axis Y (ordinate) for the number of syncytia in terms of percentage (i.e. "% number of syncytia") formed in a cell culture as compared with the value obtained in the case of the experiment (c) for "virus control", the value in this case being set always as 100 and wherein a plot drawn by a solid line (a) (— • —) shows the result obtained with the experiment (a) while a plot drawn by a dotted line (b) (— ○ —) shows the result obtained with the experiment (b).

Figure 2:
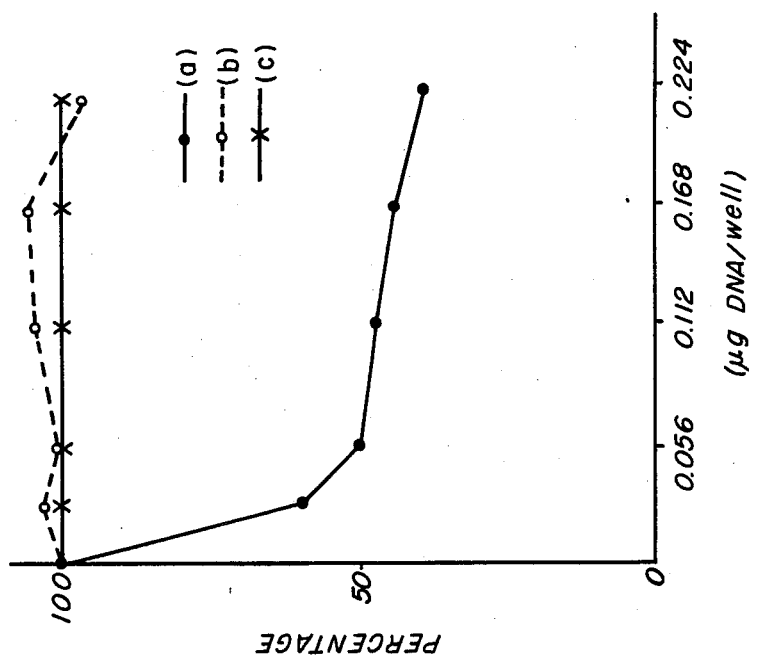
FIG. 2 is a graph showing the result of experiments which demonstrate the inhlitory effects of the oligodeoxynucleotide (the 20 A) on propagation of virus.

As shown in FIG. 2, the 20 A has an inhibitory effect on the number of syncytia produced by HSV-1. From this experiment, it can be concluded that the 20 A inhibits the syncytium formation in the presence of 4.55 mM calcium ion. Oligodeoxynucleotides which do not have any relation with the known DNA sequences of herpes simplex virus did not have any inhibitory effect. It became clear from this experiment that the minus strand of herpes simplex virus DNA *specifically* inhibits the cytopathic effect of herpes simplex virus.

EXAMPLE 11

In Example 9 the effect achieved by using the synthetic eicosamer 20 A related to the minus strand of HSV-DNA is illustrated. This experiment relates to effectiveness of cloned herpes simplex DNA. Using the pBR 322 vector containing HSV-1 DNA (1.45 megadalton, obtained by digestion of HSV-1 DNA with BamHI), it was possible to inhibit syncytium formation by HSV-1. In this experiment, HSV-1 DNA was not excised from the recombinant plasmid. The denatured and partially digested recombinant pBR 322 containing HSV-1 DNA (0.16 µg) was placed in each well of the Limbro dish as in the Example 9. The effect was examined as described in Example 9 and an inhibition of syncytium formation was observed. As a control for this experiment, DNA of pBR 322 alone was used. In this control experiment, no inhibition was found.

EXAMPLE 12

This example illustrates a synergistic effect of a mixture of the oligodeoxynucleotides.

Approximately $1.5 \times 10^5$ BHK cells were plated in each well (1.5 cm in diameter) of a Limbro dish. The cells were incubated in 5% $CO_2$ at 36° C. for 47 to 48 hours and infected with HSV-1 ($7.6 \times 10^4$ PFU/ml) in 160 µl of MEM. Infection was carried out for 3 hours at 36° C. in 5% $CO_2$. After the infection, the 20 A alone or in mixture with the 20 B (224:1) was dissolved in a solvent and 0.3 ml of this solution was applied to the cells in the presence of 4.55 mM calcium ions. The exposure of these cells to the 20 A and the 20 B was carried out for 8 hours.

On the other hand, the cells were allowed to receive the identical treatments to those described above except for the absence of the 20 A and the 20 B. This is referred to herein as virus control.

The cells were fixed, stained and the number of syncytia was counted. The results of these experiments are shown in FIG. 3 wherein the axis X (abscissa) stands for the amount of DNA in terms of µg added to each well (i.e. "µg DNA/well") and the axis Y (ordinate) for the number of syncytia in terms of percentage (i.e. "% number of syncytia") formed in a cell culture as compared with the value obtained in the case of "virus control", the value in this case being set always as 100 and wherein a plot drawn by a solid line designated as "20 A" (— ○ —) shows the result obtained with the experiment using the 20 A alone while a plot drawn by a solid line designated as "20 A + 20 B (224:1)" (— • —) shows the result obtained with the experiment using a combination of the 20 A and the 20 B in the ratio of 224:1. As shown in FIG. 3, when the mixture of the 20 A and the 20 B was used, the observed in vitro effect was stronger as compared with the case of using the 20 A alone. From this result, it is concluded that the conjoint use of minus stranded DNA corresponding to a portion having different DNA sequence of the minus stranded DNA of herpes simplex virus may significantly strengthen the effectiveness as antiviral agents.

EXAMPLE 13

This example illustrates the effect of (—) strand oligodeoxynucleotides of NS 1 on the cytopathic effect of influenza virus. The results of the examination are shown in Table 3 and the method for the examination are described below in detail.

TABLE 3

| Oligodeoxynucleotides (µg/ml) | Relative value related to the number of viable cells |
|---|---|
| 0 | 0.21 |
| 0.02 | 0.49 |
| 1.30 | 0.49 |
| 5.00 | 0.49 |

Swine Kidney Kitazato (SKK) cells ($1.5 \times 10^5/0.1$ ml) were grown in MEM containing 5% fetal calf serum and plated in each well (0.5 cm in diameter) of a microplate. The cells were incubated for 24 hours at 35.5° C. in 5% $CO_2$ atmosphere in the above medium. The medium was then removed and 100 µl of a medium containing various amounts of the oligodeoxynucleotide (20 C), were added to each well and the cells were incubated 24 hours in 5% $CO_2$ atmosphere. The solution was then removed and 50 µl of a medium containing 10 TCID50 units of Influenza A was added to each well. In addition, 50 µg of the culture medium containing various amounts of the 20 C was added to each well. The cells were further incubated for 48 hours. The medium was then removed and 100 µl of Hank's solution containing 0.1% neutral red were added to each well and the cells were incubated for 1 hour at 35.5° C. in a 5% $CO_2$ incubater. The solution was then removed and the cells were washed with 10 µl of 80% ethanol, followed by the addition of 50 µl of 0.1N HCl. The relative number of viable cells was measured by optical absorption at 577 nm with ELISA. The viable cells take up neutral red while non viable cells do not. Therefore, the higher the optical density, the higher the number of viable cells.

The following Examples 14–20 show the efficacy in vivo of using the oligodeoxynucleotides as an anti viral agent.

EXAMPLE 14

Approximately $1 \times 10^4$ PFU of HSV-1 (F strain) in 30 µl of MEM suspension were injected into the intracerebral cavities of three week old BALB/C mice. The virus suspension contained various amounts of the 20 A. In addition, 200 µl of MEM solution containing 1% penicillin, streptomycin, and 2 mM glutamic acid, and various amounts of the 20 A were injected daily for 3 days into intraperitoneal cavities starting one day after the injection with HSV-1. The percentage of mortality rate at the 7th day was calculated. The result of the experiment is shown in FIG. 4, wherein the axis X (abscissa) stands for the amount of DNA in terms of µg injected to each mouse (i.e. "µg DNA/mouse") and the axis Y (ordinate) for the mortality rate in terms of percentage as compared with that obtained in case of "control" wherein the mice received injection of the same solution but no 20 A, the mortality rate in the case of "control" being set always as 100. As shown in FIG. 4, the mortality rate was reduced depending on the amount of the 20 A administered.

The graph indicates the mortality rate expressed in terms of percentage as compared to the control mice group which did not receive any 20 A.

EXAMPLE 15

Approximately $1 \times 10^4$ PFU of HSV-1 (F strain) in 30 µl MEM solution containing various amounts of the 20 A were injected into the intracerebral cavities of 3 weeks old BALB/C mice. In addition, 200 µl of a solution containing various amounts of the 20 A, 1% penicillin and streptomycin, and 2 mM glutamic acid were injected intraperitoneally once a day starting one day after the injection of the HSV-1.

The treatment was continued for consecutive 6 days. The mortality of mice at 64 to 68 hours after the injection of the HSV-1 was examined. The results are shown in Table 4.

TABLE 4

| Dosage | Mortality of mice |
|---|---|
| — | 5/19 |
| 0.224 µg/mouse | 0/9 |
| 2.240 µg/mouse | 0/10 |

As shown in this table, in the control group, 5 mice out of the total 19 mice died without administration of the 20 A. On the other hand, mice which received either 0.224 µg of the 20 A or 2.240 µg of the 20 A did not die at this point (19 mice were treated in total in the two cases).

EXAMPLE 16

Approximately $5 \times 10^4$ PFU of HSV-1 (F strain) in 30 μl MEM solution containing various amounts of the 20 A were injected into the intracerebral cavities of 3 weeks old BALB/C mice. The mortality of the mice at 64 to 68 hours or 71 to 78 hours after the injection was examined. The results are shown in Table 5.

TABLE 5

| Dosage | Mortality between 64 and 68 hours | Mortality between 71 and 78 hours |
| --- | --- | --- |
| — | 3/10 | 3/10 |
| 1.12 μg/mouse | 0/10 | 2/10 |
| 11.2 μg/mouse | 0/10 | 0/10 |

As shown in this table, in the control group which did not receive the 20 A, 3 mice out of the total 10 mice died. On the other hand, the mortality of the mice in the group which received virus in the presence of the 20 A was highly reduced.

EXAMPLE 17

Approximately $5 \times 10^4$ PFU of HSV-1 (F strain) in 30 μl MEM solution containing various amounts of the 20 A were injected into the intracerebral cavities of 3 weeks old BALB/C mice. In addition, from the day after injection of 30 μl of MEM solution containing a given amount of the 20 A, 1% penicillin and streptomycin, and 2 mM glutamic acid were injected into the intracerebral cavities.

The treatment was continued for 2 days and the mortality of the mice was examined at various periods after the injection of the virus.

The results are shown in Table 6.

TABLE 6

| Dosage | Mortality between 64 and 68 hrs. | between 71 and 78 hrs. | between 88 and 92 hrs. |
| --- | --- | --- | --- |
| — | 1/10 | 3/10 | 7/10 |
| 1.12 μg/mouse | 0/20 | 2/20 | 5/20 |

As shown in this table, the mortality among control mice which did not receive the 20 A was significantly higher than among those mice which received the 20 A. Although the efficacy of the 20 A apparently decreases at 88 to 92 hours after the injection, the mortality was still higher among the control mice even under these conditions.

EXAMPLE 18

Approximately $1 \times 10^6$ PFU of HSV-1 (F strain) in 200 μl of MEM solution containing 1.12 μg of the 20 A were injected into the peritoneal cavities of 3 weeks old BALB/C mice.

In addition, approximately 3 or 2 hours prior to the HSV-1 injection, and one day after the injection of HSV-1, 200 μl of MEM solution containing various amounts of the 20 A were injected intraperitoneally into the infected mice. Intraperitoneal injection of the 20 A was continued for 2 days. The mortality at 211 and 259 hours after the injection of HSV-1 was examined. The results are shown in Table 7.

TABLE 7

| Dosage | Mortality at 211 hours | Mortality at 259 hours |
| --- | --- | --- |
| — | 1/10 | 2/10 |
| 0.224 μg/mouse | 0/10 | 0/10 |

As shown in this table, one out of the total 10 (at 211 hours after the injection) or 2 out of the total 10 (at 259 hours after the injection) of mice died when the 20 A was not administered. On the other hand, the mice which received 0.224 μg of the 20 A did not die under the identical conditions.

EXAMPLE 19

Cornea of 3 weeks old BALB/C mice was injured by scratching it 5 times with a sharp injection needle. Onto this wounded cornea, 30 μl of MEM solution containing 1% penicillin, streptomycin, and 2 mM glutamic acid 5% calf serum and $3 \times 10^4$ PFU of HSV-1 (F strain) were administered. The treated mice were divided into four groups (A), (B), (C) and (D) as indicated below and the eyes of these mice were examined and the results are recorded by photography.

(A) Onto the corneal membrane of these mice, 10 μl of MEM solution containing 22.4 μg of the 20 A/ml were dropped at 2 hours prior to the administration of HSV-1 (F strain). In addition, such treatment was given every other day starting from the next day after the administration of HSV-1 (F strain).

In addition, these mice received drops of a solution containing cortisone acetate (2 mg/kg of mouse body weight) at 5 hours before the injection of HSV-1 (F strain). The cortisone treatment was also continued every other day.

(B) The mice received into their eyes, 10 μl of MEM solution containing 22.4 μg of the 20 A/ml at 2 hours before the administration of HSV-1 (F strain). The treatment with the 20 A was continued every other day.

(C) The mice received 30 μl of a solution containing cortisone acetate (2 mg/kg body weight) as described in (A).

(D) The mice received on their corneal membrane, 10 μl of MEM solution at 2 hours prior to the HSV-1 (F strain) treatment. In addition, from the next day after the HSV-1 (F strain) treatment, a similar treatment with MEM solution was continued every other day.

The situation of eyes and the area surrounding the eyes of each mouse was examined with a particular attention to inflammation and closure of eyes with pathological symptoms. Examination was performed on the 4th, 7th or 12th day after the treatment. The mice belonging to group (A) and group (B) had much less pathological symptoms of eyes and the surrounding area as compared to those mice belonging to group (C) and group (D) which did not receive the 20 A.

It is further concluded that the effectiveness of the 20 A was not influenced by the administration of cortisone.

The following examples 20-22 illustrate the preparation of various types of the anti-viral agents of the present invention.

EXAMPLE 20

An oligodeoxynucleotide identical with the 20 A obtained in Example 3 is synthesized according to the triester method (using a triester of the corresponding nucleotides in liquid phase). To 2 g of the 20 A thus synthesized is added an isotonic MEM solution to a final volume of 1 liter solution for injection, and the solution was charged into ampoules to prepare the injection preparations. This injection preparation contains 2 mg of the 20 A per ml and is administered subcutaneously at a dose of 1–5 ml when a symptom is observed as near as possible to the infected part.

EXAMPLE 21

An oligodeoxynucleotide identical with the 20 B obtained in Example 4 is synthesized according to the triester method. To 10 g of the 20 B thus synthesized is added an isotonic MEM solution to a final volume of 1 liter which is a stock solution for a 1% eye drop preparation. This eye drop preparation is applied several times a day in a dose of 2–3 drops when a symptom is observed.

EXAMPLE 22

An oligodeoxynucleotide identical with the 20 A obtained in Example 3 is synthesized according to the triester method. One gram of the 20 A thus synthesized is ground to a fine powder and 999 g of purified cacao butter is then added to the fine powder. The mixture is kneaded in a water bath at 60° C. and then molded to form suppositories, each weighing 2 g.

Each suppository contains 2 mg of the 20 A and is used according to the symptom.

The following examples 23 and 24 illustrate safety of the anti-viral agent of the present invention.

EXAMPLE 23

When the 20 A in an amount of 100 μg/kg was administered to BALB/C mice intraperitoneally, no change of the test animal was observed.

EXAMPLE 24

As a test for confirming the effect described in the preceding example, the same test was carried out as described in Example 19 except that HSV-1 was not used. In this test, no difference is found between the group of test animals to which the 20 A had been administered and those to which the 20 A had not been administered.

In view of the foregoing examples, it is evident that the anti-viral agents of the present invention are safe in an effective dose of the oligo- and polydeoxynucleotides.

The following examples are included herein to indicate that in vitro protein synthesis system is indeed inhibited by hybridizing the mRNA with (−) strand oligodeoxynucleotide. These results substantiate the theoretical basis of this invention.

EXAMPLE 25

(Referential Example 1)

This example illustrates inhibition of polyphenylalanine synthesis dependent on poly U by oligodeoxyadenylic acid.

The reaction mixture (40 microliters) contained 140 micrograms of poly U, $C^{14}$ phenylalanine ($10^5$ cpm, 300 micro curie/micromole, E. coli extract (prepared according to Nirenberg and Mathaei, Proc. Nat. Acad. Sci., U.S.A. 47 1588 (1961)), 13 mM Mg acetate, 1 mM ATP, 1 mM creatine phosphate, 1 microgram of creatine phosphokinase, 10 mM Tris-HCl (pH 7.5), and various amounts of oligodeoxyadenylic acid. The reaction mixtures were placed in 1.5 ml Eppendorf tubes and incubated at 37° C. for 30 minutes. The amount of polyphenylalanine synthesized was measured by counting the radioactivity insoluble in a hot (95° C.) 10% trichloracetic acid. The counting was performed with a liquid scintillation counter. The percentage inhibition was calculated as compared to the value of polyphenylalanine synthesis in the absence of the oligodeoxyadenylic acid. The results are shown in Table 8.

TABLE 8

| Inhibitor | Dosage (micrograms) | Inhibition of poly-phenyl-alanine synthesis (%) |
|---|---|---|
| control | — | 0 |
| poly-deoxy-adenylic acid | 50 | 98 |
| oligo-deoxy-adenylic acid (10 nucleotides) | 100 | 88 |
| oligo-deoxy-adenylic acid (9 nucleotides) | 100 | 89 |
| oligo-deoxy-adenylic acid (8 nucleotides) | 100 | 15 |
| oligo-deoxy-adenylic acid (7 nucleotides) | 100 | 0 |

As shown in Table 8, the polydeoxyadenylic acid which hybridizes with polyuridylic acid is a remarkably strong inhibitor of polyphenylalanine synthesis. It can be seeem from this table that oligodeoxyadenylic acid with a chain length of more than 9 nucleotides has a strong inhibitory effect.

EXAMPLE 26

(Referential Example 2)

The experiment described below is a demonstration that oligodeoxynucleotides can inhibit eucaryotic mRNA activity by forming hybrids with that mRNA. The reaction mixture (30 μl) contains, 4.2 mM calcium phosphate, 2 mM dimethylthiothreitol (DTT), 0.08 mM of each amino acid (except for methionine), 6 mM calcium acetate, 8 mM magnesium acetate, 4.5 μg of spermidine, 0.1 μCi $^{35}$S-methionine and 10 μl of a rabbit reticulocyte extract prepared according to Jackson and Pelham (Europ. J. Biochem. 67, 247–256, 1976). The inhibitor was dissolved in 21 mM HEPES solution and added to the reaction mixture as described in Table 9.

TABLE 9

| Inhibitor | Dosage (μg) | % Inhibition of α-globin synthesis | % Inhibition of β-globin synthesis |
|---|---|---|---|
| Control | — | 0 | 0 |
| genome DNA of α-globin | 0.06 | 60 | 0 |
| genome DNA of β-globin | 0.06 | 0 | 65 |
| calf thymus DNA | 0.06 | 10 | 10 |
| 15 oligo-deoxy-nucleotide of α-globin genome DNA | 0.06 | 88 | 0 |
| 15 oligo-deoxy-nucleotide of M 13 | 0.06 | 5 | 2 |

As shown in Table 9, (−) stranded DNA of α-globin specifically inhibits the α-globin synthesis while (−) stranded DNA of β-globin specifically inhibits the β-globin synthesis. No significant inhibition was observed with calf thymus DNA. From these observations, it can be concluded that DNA of eucaryotic gen (− strand) specifically inhibits the synthesis of the protein coded by this gene. The oligodeoxynucleotide with the chain length of 15 corresponding to the $NH_2$-terminal amino acid sequence of α-globin inhibited the synthesis of α-globin. This observation indicates that single stranded DNA (− strand) with the chain length as short as 15 is sufficient for the specific inhibition of the synthesis of its respect protein. The control oligonucleotide (M 13 phage DNA with the chain length of 15 nucleotides) did not show any significant inhibitory effect.

It is understood that the preceding representative examples may be varied within the scope of the present specification both as to the sorts of virus and the coding region by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A pharmaceutical composition, consisting essentially of
   an effective antiviral amount of an oligodeoxynucleotide or polydeoxynucleotide which has a sequence which is identical to a portion of DNA which is hybridizable to messenger RNA of herpes virus, said oligodeoxynucleotide or polydeoxynucleotide being capable of hybridizing to said messenger RNA; and
   a pharmaceutically acceptable carrier.

2. The composition of claim 1, wherein said virus is herpes simplex virus.

3. The composition of claim 1, wherein said virus is herpes simplex virus-1.

4. The composition of claim 1, wherein said oligodeoxynucleotide or polydeoxynucleotide is capable of hybridizing immediate early messenger RNA of herpes simplex virus.

5. The composition of claim 1, wherein said oligodeoxynucleotide or polydeoxynucleotide can hybridize with a non-structural gene of said herpes virus.

6. The composition of claim 5, wherein said non-structural gene is ICP 4.

7. The composition of claim 1, wherein said oligodeoxynucleotide or polydeoxynucleotide has the sequence 3'-CGC.AGC.CTC.TTG.TTC.GTC.GC-5'.

8. The composition of claim 1, wherein said oligodeoxynucleotide or polydeoxynucleotide has the sequence 3'-GCA.CCC.GGG.ACC.TTT.ACC.GC-5'.

9. The composition of claim 1, in the form of an injectable solution.

10. The composition of claim 1, in the form of a topical preparation.

11. The composition of claim 1, in the form of an eye drop solution.

12. The composition of claim 1, which includes a mixture of said oligodeoxynucleotides or polydeoxynucleotides.

13. A method for treating herpes virus infections which comprises applying to a subject an effective antiviral amount of a pharmaceutical composition consisting essentially of an effective antiviral amount of an oligonucleotide or polydeoxynucleotide which has a sequence which is identical to a portion of DNA which has a hybridizable to messenger RNA of herpes virus, said oligodeoxynucleotide or polydeoxynucleotide being capable of hybridizing to said messenger RNA; and
a pharmaceutically acceptable carrier.

14. The method of claim 13, wherein said composition is topically applied to said subject.

15. The method of claim 13, wherein said composition is applied to an eye of said subject.

16. The method of claim 13, wherein said composition is injected into said subject.

17. The method of claim 13, wherein said composition is administered to said subject at a dose of from 1–20000 μg/kg/day.

18. The method of claim 13, wherein said virus is herpes simplex virus.

19. The method of claim 13, wherein said virus is herpes simplex virus-1.

20. The method of claim 13, wherein said oligodeoxynucleotide or polydeoxynucleotide is minus strand DNA.

21. The method of claim 13, wherein said oligodeoxynucleotide or polydeoxynucleotide has the sequence 3'-CGC.AGC.CTC.TTG.TTC.GTC.GC-5'.

22. A method for treating a virus infection which comprises applying to a subject an effective antiviral amount of a pharmaceutical composition consisting essentially of an effective antiviral amount of an oligodeoxynucleotide or polydeoxynucleotide which has a sequence which is identical to a portion of DNA which is hybridizable to messenger RNA of a virus selected from the group consisting of adeno virus, vaccinia virus, influenza virus, rhino virus and polio virus, said oligodeoxynucleotide or polydeoxynucleotide being capable of hybridizing to said messenger RNA and a pharmaceutically acceptable carrier or diluent.

* * * * *